(12) United States Patent
Suzuki et al.

(10) Patent No.: US 8,879,055 B1
(45) Date of Patent: Nov. 4, 2014

(54) INSPECTION METHOD AND INSPECTION APPARATUS

(71) Applicant: Lasertec Corporation, Kanagawa (JP)

(72) Inventors: Hironobu Suzuki, Kanagawa (JP); Katsuyoshi Nakashima, Kanagawa (JP); Kazuhito Yamamoto, Kanagawa (JP)

(73) Assignee: Lasertec Corporation, Kanagawa (JP)

( * ) Notice: Subject to any disclaimer, the term of this patent is extended or adjusted under 35 U.S.C. 154(b) by 0 days.

(21) Appl. No.: 14/274,919

(22) Filed: May 12, 2014

(30) Foreign Application Priority Data

May 13, 2013 (JP) ................................. 2013-101457

(51) Int. Cl.
*G01N 21/00* (2006.01)
*G01N 21/956* (2006.01)
*G01N 21/88* (2006.01)

(52) U.S. Cl.
CPC .......... *G01N 21/956* (2013.01); *G01N 21/8851* (2013.01); *G01N 2021/8887* (2013.01); *G01N 2021/95676* (2013.01)
USPC ....................... 356/237.1; 356/237.4; 356/394

(58) Field of Classification Search
CPC ............ G01N 21/956; G01N 21/8851; G01N 2012/8887; G01N 2021/95676
USPC ......... 356/237.1–237.5, 392–392; 250/559.4, 250/559.41, 559.45, 548; 382/145, 148, 382/154
See application file for complete search history.

(56) References Cited

U.S. PATENT DOCUMENTS

| | | | |
|---|---|---|---|
| 5,898,182 A * | 4/1999 | Toyama | 250/559.41 |
| 7,046,352 B1 | 5/2006 | Dayal et al. | |
| 7,664,310 B2 | 2/2010 | Emery | |
| 7,735,055 B2 * | 6/2010 | Tsutsui et al. | 716/50 |
| 7,808,629 B2 * | 10/2010 | Lim et al. | 356/237.5 |
| 7,907,270 B2 * | 3/2011 | Kusunose | 356/237.4 |
| 2003/0189703 A1 * | 10/2003 | Yonezawa et al. | 356/237.2 |
| 2006/0270072 A1 * | 11/2006 | Ikenaga et al. | 438/14 |
| 2008/0186476 A1 | 8/2008 | Kusunose | |
| 2009/0168191 A1 * | 7/2009 | Takehisa et al. | 359/665 |

FOREIGN PATENT DOCUMENTS

| | | |
|---|---|---|
| JP | 61-126455 A | 6/1986 |
| JP | 2007-132729 A | 5/2007 |
| JP | 2008-096296 A | 4/2008 |
| JP | 2008-190938 A | 8/2008 |

OTHER PUBLICATIONS

Office Action issued on Jan. 14, 2014 in the corresponding JP Patent Application 2013-101457.

* cited by examiner

*Primary Examiner* — Sang Nguyen
(74) *Attorney, Agent, or Firm* — Carrier Blackman & Associates, P.C.; Joseph P. Carrier; William D. Blackman

(57) ABSTRACT

The field of view of an objective lens is divided into two areas, and a transmission image of a photomask and a composite image obtained by optically synthesizing a transmission image and a reflection image of the photomask are picked up in parallel. A drop image generated at an edge portion of a pattern portion in the composite image is deleted by limiter processing or masking processing, or is deleted by using primary-differentiated signals of a composite image signal and a transmission image signal.

14 Claims, 11 Drawing Sheets

Fig. 2
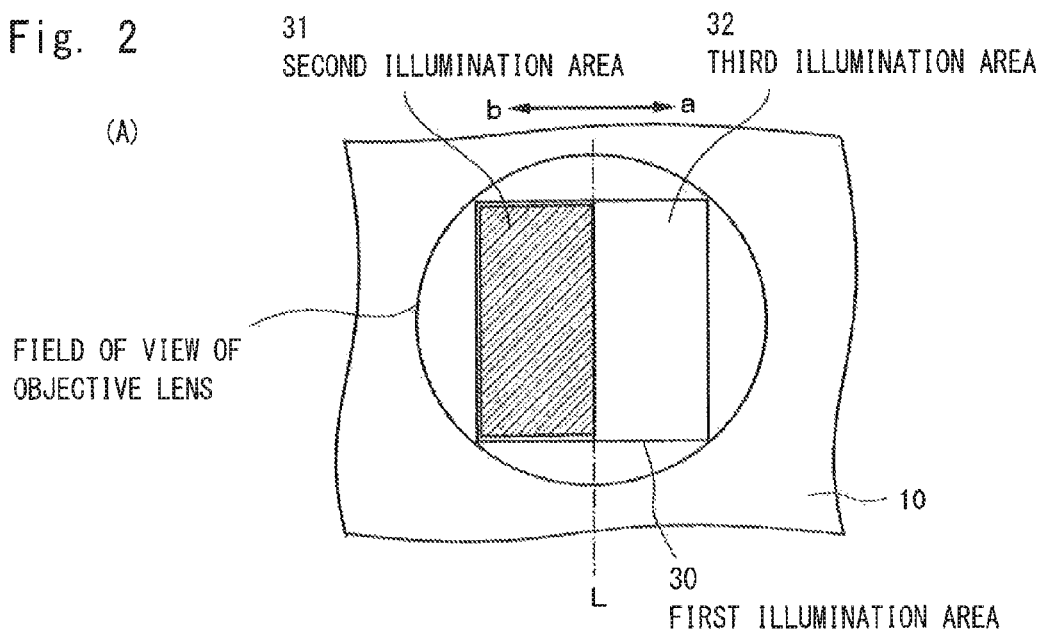
(A)
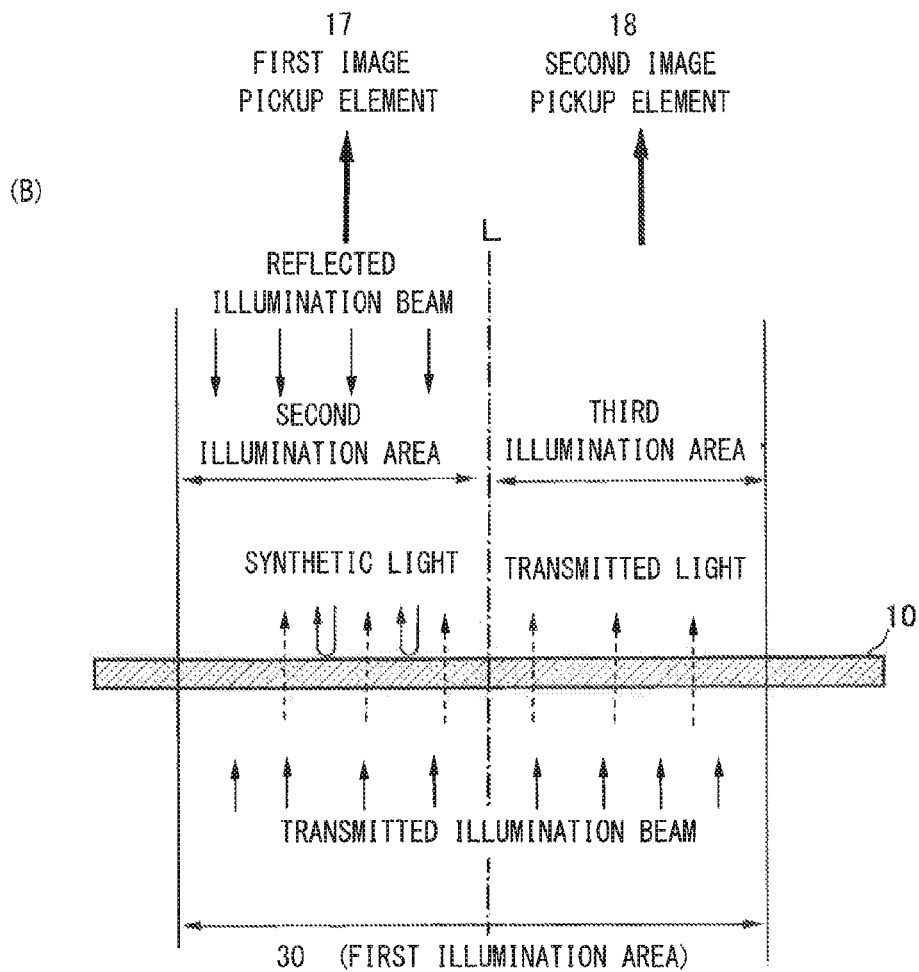
(B)

INSPECTION METHOD AND INSPECTION APPARATUS

INCORPORATION BY REFERENCE

This application is based upon and claims the benefit of priority from Japanese patent application No. 2013-101457, filed on May 13, 2013, the disclosure of which is incorporated herein in its entirety by reference.

BACKGROUND OF THE INVENTION

1. Field of the Invention

The present invention relates to an inspection method and an inspection apparatus for inspecting various photomasks such as a binary type photomask, a half-tone type photomask, and a tri-tone type photomask.

2. Description of Related Art

With the miniaturization of semiconductor devices, there is a demand for development of an inspection apparatus capable of detecting a fine defect present in a photomask with high sensitivity. As a related-art inspection apparatus that detects a defect present in a photomask, an inspection apparatus is known in which a transmission image and a reflection image of a photomask are individually picked up and a defect is detected based on the transmission image and the reflection image (see, for example, U.S. Pat. No. 7,664,310). Such a known inspection apparatus has a configuration in which an illumination beam output from a light source is projected toward a pattern forming surface of a photomask; the reflected beam reflected by the pattern forming surface of the photomask is received by a first detector; and the transmitted beam transmitted through the photomask is received by a second detector that is disposed on the opposite side of the light source. Output signals output from the first and second detectors are supplied to a processor. In the processor, Cartesian coordinates are provided by using an intensity T of the transmitted light and an intensity R of the reflected light, and T-R data on various photomasks are accumulated to form a T-R map. A portion of data outside a range defined by the envelope of the generated T-R map is determined to be defective.

Another known inspection apparatus has the following configuration. In the inspection apparatus, a reflected illumination beam is projected toward a pattern forming surface of a photomask to be inspected and a transmitted illumination beam is projected toward the back surface thereof; a composite image obtained by optically adding a transmission image and a reflection image of a region of the photomask is picked up; and a defect is detected based on the composite image (see, for example, U.S. Pat. No. 7,046,352 and Japanese Unexamined Patent Application Publication Nos. 2007-132729 and 2008-96296).

As a still further inspection apparatus, an inspection apparatus is known in which a transmission image of a photomask and a composite image of a transmission image and a reflection image are picked up, and a defect is detected based on the transmission image and the composite image (see, for example, Japanese Unexamined Patent Application Publication No. 2008-190938). In such a known inspection apparatus, the field of view of an objective lens is divided into two regions. The transmission image of the photomask is formed in one of the divided regions of the field of view, and the composite image of the transmission image and the reflection image is formed in the other region of the field of view.

A photomask has a structure in which a light-shielding pattern of a molybdenum silicide film or a metallic chromium film is formed on a quartz substrate. The pattern has been miniaturized with the miniaturization of devices. However, with the miniaturization of the pattern, the diffraction effect on an edge portion of the pattern becomes more prominent, and there is a strong demand for ameliorating the deterioration in detection sensitivity at the pattern edge portion. Specifically, the pattern edge portion forms a kind of optical step. Accordingly, illumination light incident in the vicinity of the pattern edge is affected by the diffraction effect due to the step and reflected light output from the pattern is not incident on a photodetector, with the result that a malfunction occurs due to a decrease in resolution of the edge portion of the pattern. In particular, transmitted illumination light is relatively slightly affected by the diffraction effect due to the pattern edge, while reflected illumination light is greatly affected by the diffraction effect. As a result, in the inspection apparatus, which individually picks up a reflection image and a transmission image to detect a defect, the resolution of the reflection image significantly decreases and a malfunction occurs due to the deterioration in detection sensitivity with respect to a foreign matter defect present in the vicinity of the edge on the pattern.

In the inspection apparatus that projects illumination beams toward the front surface and the back surface of a photomask at the same time and picks up the composite image of the transmission image and the reflection image of the photomask, the transmitted light transmitted through the photomask is partially incident on the photodetector that receives the reflected light by the diffraction effect. This is advantageous in that the effect due to the diffraction effect at the edge of the light-shielding pattern is reduced and in that minute foreign matter defects present in the vicinity of the edge of the pattern can be satisfactorily detected. Further, the transmission image of the photomask is relatively slightly affected by the diffraction effect, which is beneficial for inspection of a defect present in a light-transmitting portion (an area in which no pattern is formed). However, there is a drawback that the diffraction effect cannot also be avoided in the composite image, which is obtained by synthesizing the transmission image and the reflection image, and a low-luminance image (hereinafter, referred to as "a drop image") in which the luminance of the image is locally reduced in the vicinity of the edge of the pattern due to the diffraction effect is formed. Such drop images are prominently generated during an inspection of a half-tone type phase shift mask (EPSM). The low-luminance image causes a pseudo defect. When a threshold level for detection of a defect is set to a high level, the low-luminance image is detected as a pseudo defect and a malfunction occurs in which a normal region is determined as a defect. On the other hand, when the threshold level is set to a low level so as to prevent the drop image from being detected as a defect, a minute defect to be detected cannot be detected and a malfunction occurs in which the sensitivity for detection of a defect deteriorates.

Furthermore, in the inspection apparatus that detects a defect by using the composite image, it is necessary to set an appropriate amount of reflected light at the pattern edge. Therefore, the following problem arises. That is, constraints are imposed on the intensity of the transmitted illumination light and the illumination intensity of the transmitted illumination light is shifted from an optimum illumination intensity. Specifically, when it is primarily intended to detect a foreign matter defect on a pattern, the intensity of the transmitted illumination light is shifted from an optimum value. Further, when it is primarily intended to detect a defect in the light-transmitting portion (quartz substrate), the intensity of the transmitted illumination light is set to the optimum value, but a malfunction occurs in which the sensitivity for detection of a defect in the vicinity of the edge portion of the pattern portion deteriorates.

The inspection apparatus that individually picks up a transmission image and a composite image of a transmission image and a reflection image of a photomask has an advantage that a defect inspection using the transmission image of the photomask and a defect inspection using the composite image can be individually carried out. In other words, since the diffraction effect due to the pattern edge on the transmitted illumination light is relatively small, a defect present in the light-transmitting portion can be detected with high sensitivity even when the pattern is miniaturized. Further, the resolution in the pattern edge portion of the composite image is relatively high with respect to a defect present in the pattern portion, which is advantageous in that a defect present in the vicinity of the edge portion of the pattern can be detected with high detection sensitivity. There is another advantage that the transmission image inspection and the composite image inspection can be carried out by setting an optimum illumination light intensity. This makes it possible to achieve an advantage that a defect inspection can be carried out more satisfactorily than in the above-mentioned inspection apparatus that carries out the inspections based only on the composite image.

However, the diffraction effect due to the pattern edge causes the low-luminance image (drop image), in which the luminance is locally reduced in the vicinity of the edge of the pattern portion in the composite image, to be formed, and especially, the low-luminance image is prominently generated during the inspection of the EPSM. In this regard, the following problem arises. That is, a pseudo defect is generated due to the presence of the low-luminance image, or the presence of the low-luminance image makes it difficult to set the detection sensitivity to a high level. Therefore, if a defect detection method in which the effect of the drop image is eliminated can be achieved, a defect present in the vicinity of the edge of the pattern portion can be detected with high sensitivity even when the light-shielding pattern is miniaturized.

An object of the present invention is to provide a defect inspection method and an inspection apparatus in which the diffraction effect due to a pattern edge is reduced.

Another object of the present invention is to provide an inspection method and an inspection apparatus which are not affected by a drop image formed in the vicinity of a pattern edge in a defect inspection in which a transmission image and a composite image obtained by synthesizing a transmission image and a reflection image of a photomask are individually picked up and a defect is detected based on the transmission image and the composite image.

SUMMARY OF THE INVENTION

A first aspect of the present invention is an inspection method that inspects a photomask having a pattern portion and a light-transmitting portion, the pattern portion and the light-transmitting portion being formed on a transparent substrate, the inspection method including:

forming a transmission image of a photomask to be inspected;

forming a composite image obtained by optically synthesizing a transmission image and a reflection image of the photomask, the composite image being set so as to satisfy $b2<b1$, when a luminance value of an image of the pattern portion is $b1$ and a luminance value of an image of the light-transmitting portion is $b2$;

a limiter step of deleting, in the composite image, an image portion having a luminance value equal to or smaller than a predetermined luminance value $b0$ that satisfies $b2<b0<b1$, or uniformly converting the image portion into a signal representing a luminance value equal to or smaller than the luminance value $b1$; and detecting a defect based on the composite image subjected to the limiter processing and the transmission image.

According to the present invention, the field of view of an objective lens is divided into two areas, and the transmission image and the composite image of the photomask are individually picked up. An important feature of the present invention resides in that an illumination optical system is adjusted so as to provide a difference between the luminance value of the image of the pattern portion and the luminance value of the image of the light-transmitting portion in the composite image. Specifically, when the luminance value of the image of the pattern portion is $b1$ and the luminance value of the image of the light-transmitting portion is $b2$, the illumination optical system is set so as to satisfy $b2<b1$. In this manner, the provision of a difference in luminance value between the image of the pattern portion and the image of the light-transmitting portion makes it possible to delete a drop image by the limiter processing in the signal processing. A signal processing device performs limiter processing on the composite image to delete the image portion corresponding to the transmission image and the drop image. Further, a defect present in the pattern portion is detected based on the composite image, and a defect present in the light-transmitting portion is detected based on the transmission image. In the composite image subjected to the limiter processing, the diffraction effect is reduced. Consequently, a defect present in the pattern portion, in particular, a defect present in the vicinity of the edge of the pattern can be detected with high resolution. Note that the term "image" used herein refers not only to a two-dimensional image of a photomask, but also to a one-dimensional image formed by a movement of a stage in a main scanning direction.

A second aspect of the present invention is an inspection method that inspects a photomask having a pattern portion and a light-transmitting portion, the pattern portion and the light-transmitting portion being formed on a transparent substrate, the inspection method including:

forming a transmission image of a photomask to be inspected;

forming a composite image obtained by optically synthesizing a transmission image and a reflection image of the photomask, the composite image being set so as to satisfy $b2<b1$, when a luminance value of an image of the pattern portion is $b1$ and a luminance value of an image of the light-transmitting portion is $b2$;

a limiter step of deleting, in the composite image, an image portion having a luminance value equal to or smaller than a predetermined luminance value $b0$ that satisfies $b2<b0<b1$, or uniformly converting the image portion into a signal representing a luminance value equal to or smaller than the luminance value $b1$;

forming an added composite image by adding the composite image subjected to limiter processing and the transmission image; and a defect detection step of detecting a defect by comparing the added composite image with a first threshold.

According to the present invention, a signal processing device performs limiter processing on the composite image to delete the image portion corresponding to the transmission image and the drop image. After that, the composite image, from which the transmission image is deleted, and the transmission image, which is individually picked up, are electrically added and synthesized, thereby forming the added composite image. Since the added composite image includes the image of the pattern portion and the image of the light-transmitting portion of the photomask, defects present in the pattern portion and the light-transmitting portion can be detected with high sensitivity by comparing the luminance value of the added composite image with a threshold. In particular, in the composite image, a difference is formed between the luminance value of the image of the pattern portion and the luminance value of the image of the light-transmitting portion. This makes it possible to delete the drop image formed at the edge portion of the pattern portion by performing limiter processing and to carry out a defect inspection in which the diffraction effect due to the pattern edge is reduced. Further, since the composite image obtained by optically synthesizing the reflection image and the transmission image has a high resolution in the vicinity of the edge portion of the pattern portion, a defect in the pattern portion can be detected with high resolution. Furthermore, the transmission image is relatively slightly affected by the diffraction, so that a defect in the light-transmitting portion can also be detected with high detection sensitivity.

A third aspect of the present invention is an inspection method that inspects a photomask having a pattern portion and a light-transmitting portion, the pattern portion and the light-transmitting portion being formed on a transparent substrate, the inspection method including:

forming a transmission image of a photomask to be inspected;

forming a composite image obtained by optically synthesizing a transmission image and a reflection image of the photomask, the composite image being set so as to satisfy $b2<b1$, when a luminance value of an image of the pattern portion is $b1$ and a luminance value of an image of the light-transmitting portion is $b2$;

a first masking step of masking, in the transmission image, an image portion having a luminance value equal to or smaller than a predetermined luminance value $a0$ that satisfies $a2<a0<a1$, when a luminance value of an image of the light-transmitting portion is $a1$ and a luminance value of an image of the pattern portion is $a2$;

a second masking step of masking, in the composite image, an image portion having a luminance value equal to or smaller than a predetermined luminance value $b0$ that satisfies $b2<b0<b1$;

a first defect detection step of comparing an image signal subjected to the first masking processing with a first threshold;

a second defect detection step of comparing an image signal subjected to the second masking processing with a second threshold.

According to the present invention, the use of masking processing allows the image of the pattern portion to be selectively extracted based on the composite image, and allows the image of the light-transmitting portion to be selectively extracted based on the transmission image. Specifically, in the composite image, a difference is provided between the luminance value of the image of the pattern portion and the luminance value of the image of the light-transmitting portion, which makes it possible to selectively retrieve only the image of the pattern portion from the composite image. As a result, it is possible to carry out a defect inspection which is relatively slightly affected by the diffraction effect and is not affected by any drop image, while utilizing the advantage of the composite image. Further, such an inspection algorithm has an advantage that the defect inspection for the pattern portion and the defect inspection for the light-transmitting portion are individually carried out.

A fourth aspect of the present invention is an inspection method that inspects a photomask having a pattern portion and a light-transmitting portion, the pattern portion and the light-transmitting portion being formed on a transparent substrate, the inspection method including:

picking up a transmission image of a photomask to be inspected and forming a transmission image signal;

forming a composite image signal by picking up a composite image obtained by optically synthesizing a transmission image and a reflection image of the photomask, the composite image being set so as to satisfy $b2<b1$, when a luminance value of an image of the pattern portion is $b1$ and a luminance value of an image of the light-transmitting portion is $b2$;

forming first and second primary-differentiated signals by performing primary differentiation processing on the composite image signal and the transmission image signal;

forming first and second binarized signals by performing binarization processing on the first and second primary-differentiated signals;

a first logical operation step of performing a first logical operation on the first binarized signal by using the second binarized signal as a gate signal, setting the first binarized signal to a logic "0" when the second binarized signal represents a logic "1", and outputting the first binarized signal as a defect detection signal; and a second logical operation step of performing a second logical operation on the second binarized signal by using the first binarized signal as a gate signal, setting the second binarized signal to a logic "0" when the first binarized signal represents the logic "1", and outputting the second binarized signal as the defect detection signal.

According to the present invention, the primary differentiation processing is performed on the composite image signal and the transmission image signal, and a variation in luminance value due to a defect and a variation in luminance value due to the edge portion of the pattern portion are detected. Subsequently, signal processing for eliminating the variation in luminance value due to the edge portion of the pattern portion is performed. This makes it possible to detect a defect based on the primary-differentiated signals of the composite image signal and the transmission image signal.

A fifth aspect of the present invention is an inspection apparatus that inspects a photomask having a pattern forming surface on which a pattern portion and a light-transmitting portion are formed, and a back surface opposed to the pattern forming surface, the inspection apparatus including:

an illumination optical system including: a transmitted illumination optical system that projects a transmitted illumination beam toward a back surface of a photomask to be inspected and illuminates a first area of the photomask; and a reflected illumination optical system that projects a reflected illumination beam toward an element forming surface of the photomask and illuminates a second area of the photomask, the second area being smaller than the first area and overlapping the first area in an optical axis direction;

a detection system including: a first image pickup element that receives synthetic light of reflected light and transmitted light output from the second area of the photomask and picks up a composite image of a transmission image and a reflection image of the photomask; and a second image pickup element that receives transmitted light output from a third area of the photomask and picks up a transmission image of the photomask, the third area being a remaining area of the first area excluding the second area; and a signal processing device that is coupled to the detection system processes an image signal output from the detection system, and outputs data indicating a defect.

The transmitted illumination optical system and the reflected illumination optical system are set so as to satisfy b2<b1, when a luminance value of an image of the pattern portion of the composite image is b1 and a luminance value of an image of the light-transmitting portion is b2.

The signal processing device includes: a limiter processing unit that performs limiter processing on an image signal output from the first image pickup element to delete a signal portion having a luminance value equal to or smaller than a luminance value b0 that satisfies b2<b0<b1, or uniformly convert the signal portion into a signal having a luminance value equal to or smaller than a luminance value b1; a dilation processing unit that performs, for the image signal output from the second pickup element, dilation processing on an edge of an image corresponding to the light-transmitting portion; an addition unit that adds a signal subjected to the limiter processing and a signal subjected to the dilation processing, and outputs an added composite signal; and a comparison unit that compares the added composite signal with a threshold.

A sixth aspect of the present invention is an inspection apparatus that inspects a photomask having a pattern forming surface on which a pattern portion and a light-transmitting portion are formed, and a back surface opposed to the pattern forming surface, the inspection apparatus including:

an illumination optical system including: a transmitted illumination optical system that projects a transmitted illumination beam toward a back surface of a photomask to be inspected, and illuminates a first area of the photomask; and a reflected illumination optical system that projects a reflected illumination beam toward an element forming surface of the photomask, and illuminates a second area of the photomask, the second area being smaller than the first area and overlapping the first area in an optical axis direction;

a detection system including: a first image pickup element that receives synthetic light of reflected light and transmitted light output from the second area of the photomask, and picks up a composite image of a transmission image and a reflection image of the photomask; and a second image pickup element that receives transmitted light output from a third area of the photomask and picks up a transmission image of the photomask, the third area being a remaining area of the first area excluding the second area; and a signal processing device that is coupled to the detection system, processes an image signal output from the detection system, and outputs data indicating a defect.

The transmitted illumination optical system and the reflected illumination optical system are set so as to satisfy b2<b1, when a luminance value of an image of the pattern portion of the composite image is b1 and a luminance value of an image of the light-transmitting portion is b2.

The signal processing device includes: a first masking unit that masks, in the transmission image, an image portion having a luminance value equal to or smaller than a predetermined luminance value a0 that satisfies a2<a0<a1, when a luminance value of an image of the light-transmitting portion is a1 and a luminance value of an image of the pattern portion is a2;

a second masking unit that masks, in the composite image, an image portion having a luminance value equal to or smaller than a predetermined luminance value b0 that satisfies b2<b0<b1;

a first defect detection unit that compares an image signal subjected to the first masking processing with a first threshold; and a second defect detection unit that compares an image signal subjected to the second masking processing with a second threshold.

A seventh aspect of the present invention is an inspection apparatus that inspects a photomask having a pattern forming surface on which a pattern portion and a light-transmitting portion are formed, and a back surface opposed to the pattern forming surface, the inspection apparatus including:

an illumination optical system including: a transmitted illumination optical system that projects a transmitted illumination beam toward a back surface of a photomask to be inspected, and illuminates a first area of the photomask; and a reflected illumination optical system that projects a reflected illumination beam toward an element forming surface of the photomask, and illuminates a second area of the photomask, the second area being smaller than the first area and overlapping the first area in an optical axis direction;

a detection system including: a first image pickup element that receives synthetic light of reflected light and transmitted light output from the second area of the photomask, and picks up a composite image of a transmission image and a reflection image of the photomask; and a second image pickup element that receives transmitted light output from a third area of the photomask and picks up a transmission image of the photomask, the third area being a remaining area of the first area excluding the second area; and a signal processing device that is coupled to the detection system, processes an image signal output from the detection system, and outputs data indicating a defect.

The transmitted illumination optical system and the reflected illumination optical system are set so as to satisfy b2<b1, when a luminance value of an image of the pattern portion of the composite image is b1 and a luminance value of an image of the light-transmitting portion is b2.

The signal processing device includes: first and second differentiation processing units that respectively form first and second primary-differentiated signals by performing primary differentiation processing on a composite image signal and a transmission image signal;

first and second binarization processing units that respectively form first and second binarized signals by performing binarization processing on the first and second primary-differentiated signals;

a first logical operation unit that performs a first logical operation on the first binarized signal by using the second binarized signal as a gate signal, setting the first binarized signal to a logic "0" when the second binarized signal represents a logic "1", and outputting the first binarized signal as a defect detection signal; and a second logical operation unit that performs a second logical operation on the second binarized signal by using the first binarized signal as a gate signal, setting the second binarized signal to the logic "0" when the first binarized signal represents the logic "1", and outputting the second binarized signal as the defect detection signal.

According to the present invention, the composite image obtained by optically synthesizing the transmission image and the reflection image of the photomask and the transmission image are picked up in parallel, and the signal processing for deleting the drop image generated at the edge portion of the pattern portion is performed on the composite image, thereby making it possible to carry out a defect inspection that is not affected by the drop image generated due to the diffraction effect. Further, the composite image and the transmission image can be individually picked up, and a defect present in the pattern portion is detected based on the composite image and a defect present in the light-transmitting portion is detected based on the transmission image. Consequently, the defect detection in which the effect of diffraction is reduced can be achieved. In particular, in the composite image, the diffraction effect is reduced, with the result that a defect present in the vicinity of the edge of the pattern can be detected with high resolution.

The above-mentioned and other objects, features, and advantages of the present invention will be fully understood from the following detailed description and the accompanying drawings. The accompanying drawings are for illustration only and are not intended to limit the present invention.

BRIEF DESCRIPTION OF THE DRAWINGS

FIGS. 2(A) and 2(B) are diagrams showing illumination areas formed by transmitted illumination light and reflected illumination light;

DESCRIPTION OF THE EXEMPLARY EMBODIMENTS

An inspection method and an inspection apparatus according to the present invention are capable of detecting defects present in various photomasks such as a binary type photomask, a half-tone type phase shift mask, a tri-tone type phase shift mask, and a Levenson type phase shift mask. In particular, since a composite image of a transmission image and a reflection image is picked up, the effect of diffraction due to pattern edges is reduced and a defect present in the vicinity of the edge of the pattern can be detected with high detection sensitivity. In the following description, a single die inspection mode for inspecting a photomask in which a single die is formed on a quartz substrate, which is a transparent substrate, is illustrated as an example. The present invention can also be applied to a die-to-die inspection mode and a die-to-database inspection mode.

Figure 1:
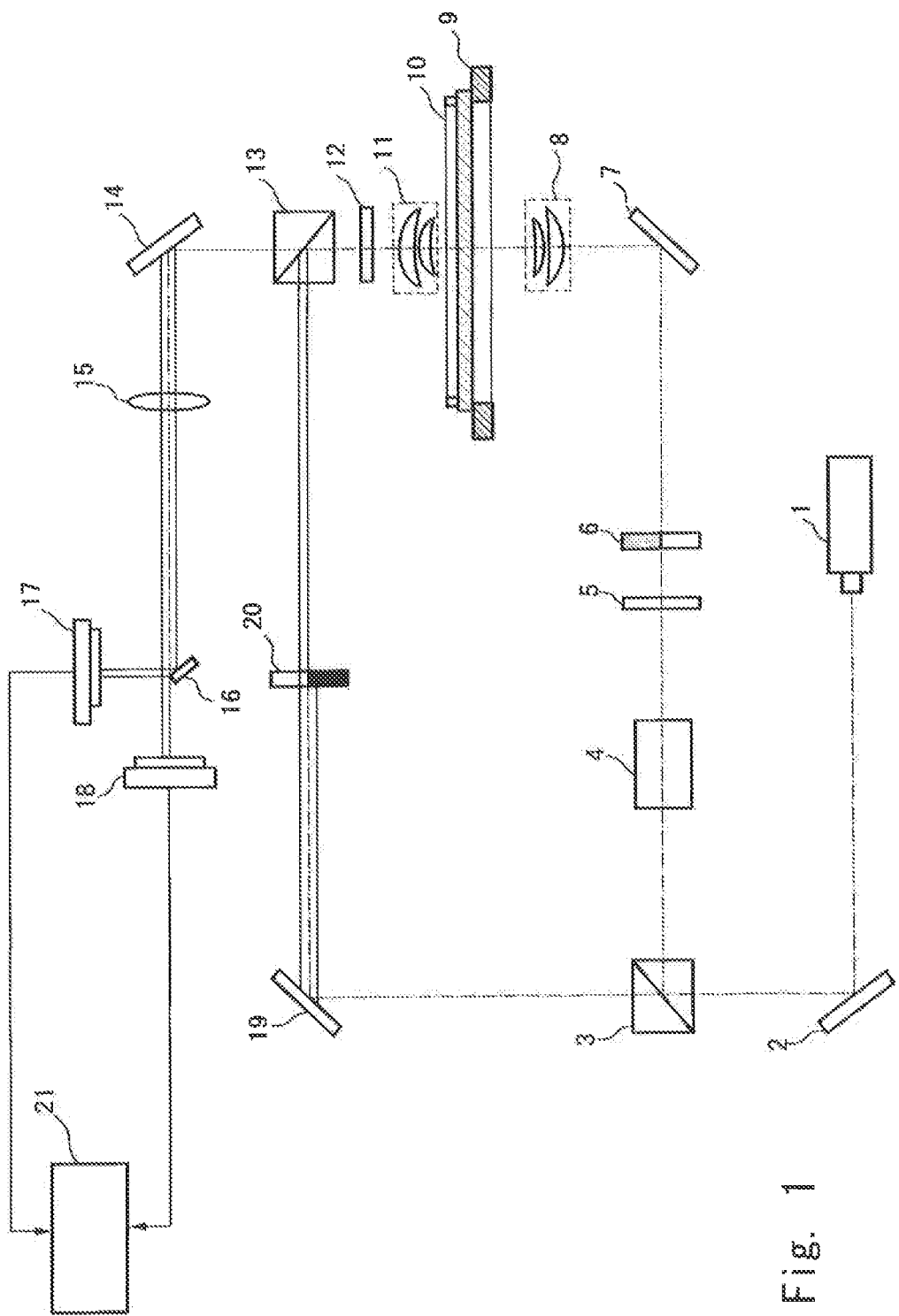
FIG. 1 is a diagram showing an example of an optical system of an inspection apparatus according to the present invention.

FIG. 1 is a diagram showing an example of an optical system of the inspection apparatus according to the present invention. A laser light source 1 is used as an illumination light source. A laser beam output from the laser light source 1 is reflected by a total reflection mirror 2 through a speckle pattern reduction device (not shown) and is incident on a first beam splitter 3. A laser beam reflected by the first beam splitter 3 forms a transmitted illumination beam, and a laser beam transmitted through the first beam splitter 3 forms a reflected illumination beam. The transmitted illumination beam passes through an attenuator 4 and a ¼ wave plate 5 and is incident on an ND filter 6. This ND filter is replaceably mounted, and functions as a means for adjusting the intensity of a beam portion incident on one half of the field of view of an objective lens. In other words, the ND filter 6 functions to adjust the luminance value of the transmission image in the composite image, and is capable of adjusting the amount of illumination light for transmitted illumination depending on the intended use of the inspection. For example, the luminance value of an image of a light-transmitting portion in a composite image can be adjusted by preparing a plurality of ND filters having different transmittances and replacing the ND filters. Thus, the replacement of the ND filters makes it possible to adjust the difference between the luminance value of an image of a pattern portion and the luminance value of an image of a light-transmitting portion in the composite image. The transmitted illumination beam output from the ND filter 6 is reflected by a total reflection mirror 7 and is incident on a condensing lens 8.

The transmitted illumination beam is incident on the back surface of a photomask 10 to be inspected, which is disposed on a stage 9, and forms a first illumination area on the back surface of the photomask. The illumination area will be described later. The stage 9 is composed of an XY stage, and moves in a zigzag manner in a main scanning direction and a sub-scanning direction perpendicular to the main scanning direction. The transmitted light transmitted through the photomask 10 is condensed by an objective lens 11 and is transmitted through a ¼ wave plate 12 and a second beam splitter 13, and is then incident on a total reflection mirror 14. Further, the light is reflected by the total reflection mirror 14 and passes through an imaging lens 15, and is then incident on a field-of-view division mirror 16. Part of the transmitted light is reflected by the field-of-view division mirror and is incident on a first image pickup element 17, and the rest of the transmitted light passes through the field-of-view division mirror and is incident on a second image pickup element 18. Each of the image pickup elements may be composed of a TDI sensor. The direction in which light receiving elements of the TDI sensor are arranged is set to be perpendicular to the main scanning direction (main movement direction) of the stage.

The laser beam transmitted through the first beam splitter 3 forms the reflected illumination beam. The reflected illumination beam is reflected by a total reflection mirror 19 and is incident on a field stop 20. The field stop blocks a beam portion of one half of the reflected illumination beam, and allows only a beam portion of the other half to pass. The reflected illumination beam output from the field stop is reflected by the second beam splitter 13 and is incident on the element forming surface of the photomask 10 through the ¼ wave plate 12 and the objective lens 11, thereby forming a second illumination area. As shown in FIGS. 2A and 2B, the second illumination area is set to have an area that is half the area of the first illumination area formed by the transmitted illumination beam, and is formed so as to overlap the first illumination area. The reflected beam reflected on the front surface (element forming surface) of the photomask is condensed by the objective lens 11, passes through the ¼ wave plate 12, and is incident on the second beam splitter 13. Further, the reflected beam is transmitted through the second beam splitter 13 and is incident on the total reflection mirror 14. Furthermore, the beam passes through the imaging lens 15 and the field-of-view division mirror 16 and is incident on the second image pickup element 18. Image signals output from the first and second image pickup elements are supplied to a signal processing device 21. The signal processing device 21 uses the image signals to detect a defect present in the photomask.

FIGS. 2A and 2B are diagrams showing the illumination areas formed by the transmitted illumination light and the reflected illumination light which are projected onto the photomask. FIG. 2A shows the illumination areas when viewed along an optical axis direction of the objective lens. FIG. 2B is a diagram showing a plane including the optical axis of the objective lens. As shown in FIGS. 2A and 2B, the inspection apparatus according to the present invention includes a reflected illumination optical system which projects illumination light for reflection inspection toward the photomask from the front surface side, and a transmitted illumination optical system which projects illumination light for transmission inspection toward the photomask from the back surface side. As shown in FIG. 2B, the transmitted illumination beam output from the transmitted illumination optical system forms a first illumination area 30 on the photomask, and the reflected illumination light output from the reflected illumination optical system forms a second illumination area 31 so as to overlap the first illumination area on the photomask. The second illumination area is set to have an area that is half the area of the first illumination area. The first illumination area is divided into two areas by a field-of-view division line L. One of the divided areas forms the second illumination area on which the reflected illumination light is incident, and the other of the divided areas forms a third illumination area 32 on which only the transmitted illumination light is incident.

The transmitted illumination beam is incident on the second illumination area 31 of the photomask to be inspected from the back surface side, and the reflected illumination beam is incident on the second illumination area 31 from the front surface side. Accordingly, the second illumination area is illuminated by the reflected illumination light and the transmitted illumination light at the same time. Thus, in the second illumination area, the reflected light reflected on the front surface of the photomask and the transmitted light transmitted through the photomask are output. Further, the transmitted illumination beam is incident on the third illumination area 32 from the back surface side, and the third illumination area 32 is illuminated only by the transmitted illumination light. Accordingly, only the transmitted beam transmitted through the photomask is output from the third illumination area.

The field-of-view division mirror 16 functions to separate the synthetic light output from the second illumination area from the transmitted light output from the third illumination area. Specifically, the transmitted light output from the third illumination area of the photomask is reflected by the field-of-view division mirror 16 and is incident on the first image pickup element 17. The synthetic light of the reflected light and the transmitted light output from the second illumination area directly passes through the field-of-view division mirror and is incident on the second image pickup element 18. Accordingly, only the transmitted light transmitted through the photomask is incident on the first image pickup element 17, and the transmission image of the photomask is picked up. The reflected light reflected by the photomask and the transmitted light transmitted through the photomask are incident on the second image pickup element 18, and the second image pickup element 18 functions to optically add the transmitted light and the reflected light, which are output from the photomask, and detects the synthetic light obtained by optically adding the transmitted light and the reflected light. That is, the light detected by the second image pickup element 18 is light obtained by optically adding the reflected light and the transmitted light, and the second image pickup element functions to optically add the transmission image and the reflection image of the photomask. Accordingly, the second image pickup element 18 picks up the composite image of the transmission image and the reflection image of the photomask.

A movement of the stage allows the photomask to move in directions indicated by "a" and "b" which are perpendicular to an adjacent line between the two illumination areas 31 and 32. Accordingly, the photomask is, for example, first scanned with the transmitted illumination beam and is further scanned with the synthetic illumination beam after a lapse of a predetermined period of time. In the case of moving in the reverse direction, the photomask is scanned with the synthetic illumination beam and is further scanned with the transmitted illumination beam after a lapse of a predetermined period of time.

Figure 3:
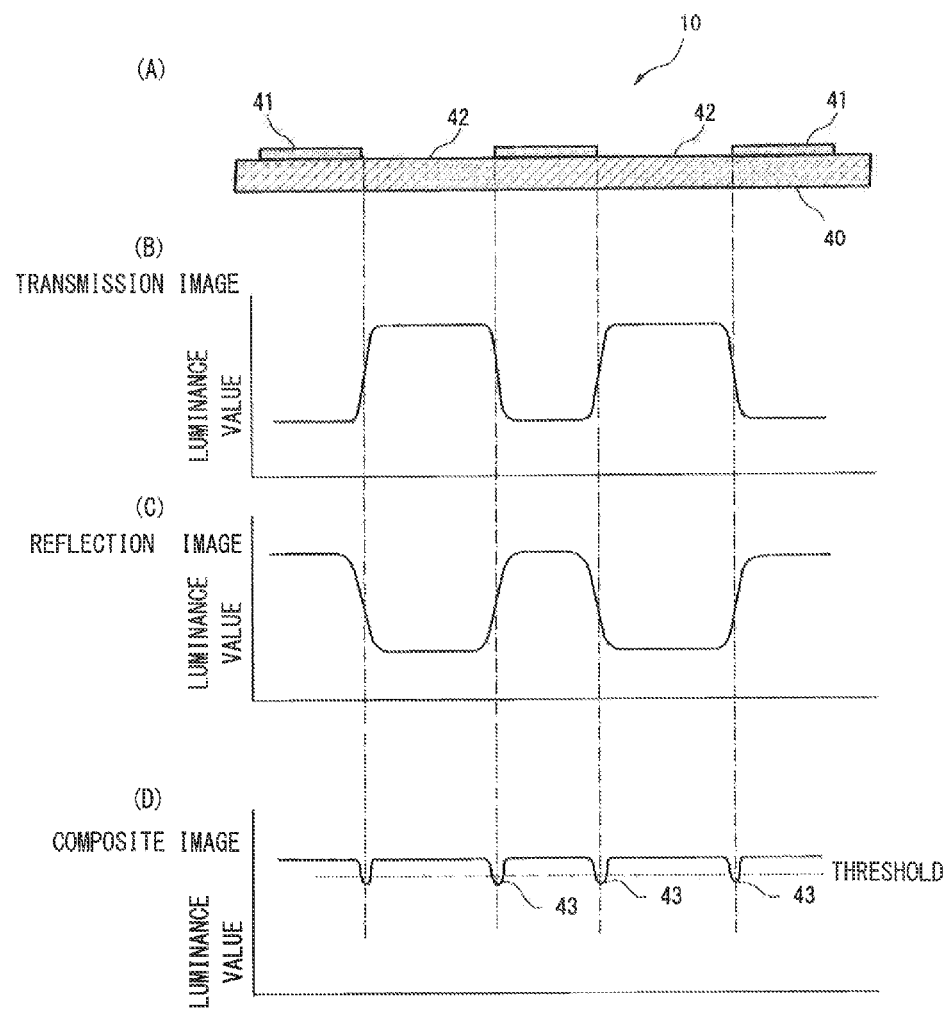
FIGS. 3(A) to 3(D) are diagrams diagrammatically showing a transmission image, a reflection image, and a composite image of a photomask.

FIG. 3A schematically shows the structure of the photomask, and FIGS. 3B to 3D diagrammatically show the transmission image, the reflection image, and the composite image, respectively, of the photomask. As shown in FIG. 3A, the photomask includes a quartz substrate (transparent substrate) 40, and pattern portion 41 that is formed of a light-shielding pattern of a molybdenum silicide film or a chromium film is formed on the transparent substrate 40. Specifically, a binary type photomask has a pattern portion formed of a chromium film; a half-tone type phase shift mask has a pattern portion formed of a half-tone film of molybdenum silicide having a transmittance of about 8%; a tri-tone type photomask has a pattern portion formed of a half-tone film and a pattern portion formed of a chromium film on the half-tone film; and a Levenson type phase shift mask has a pattern portion formed of a recess that is formed by etching. An area in which the chromium film or half-tone film is not formed forms a light-transmitting portion 42.

FIG. 3B shows the transmission image obtained so that the transmitted illumination beam is projected toward the back surface of the photomask and is picked up by the image pickup element. FIG. 3C shows the reflection image picked up by projecting the reflected illumination beam toward the pattern forming surface. FIG. 3D shows the composite image picked up by projecting the transmitted illumination beam and the reflected illumination beam at the same time by using a half-tone type phase shift mask (EPSM) as a photomask to be inspected. The term "composite image" refers to an image picked up by setting an illumination system so that the luminance value of the image of the pattern portion and the luminance value of the image of the light-transmitting portion are equal to each other. Since the transmission image and the reflection image are affected by a diffraction effect due to the edges of the pattern portion, the luminance value at the edge of the pattern portion does not vary in a step manner, but instead varies smoothly. Especially, the reflection image is greatly affected by the diffraction effect, and the luminance value at the edge portion of the pattern portion smoothly varies.

In the composite image of the transmission image and the reflection image shown in FIG. 3D, the luminance value at the edge portion of the pattern decreases due to the diffraction effect, with the result that a drop image 43 as shown in FIG. 3D is formed at the edge portion of the pattern portion. Since the drop image 43 is formed, when a threshold comparison inspection for comparing the luminance value of the composite image with a threshold is carried out, a pseudo defect occurs as a result of determining the drop image as a defect. When the threshold is set to a small value so as to prevent the drop image from being detected, a situation occurs in which a defect to be detected cannot be detected. For this reason, a defect inspection that is not affected by any drop image is required.

For the defect inspection that is not affected by any drop image, the following three inspection algorithms are used in the present invention.

(Inspection Algorithm 1)

Limiter processing is performed on the composite image to delete the drop image and the transmission image. The transmission image subjected to dilation processing is added to the composite image obtained after the limiter processing, to thereby form an added composite signal. The added composite signal is compared with a threshold to thereby detect a defect.

(Inspection Algorithm 2)

Masking processing is performed on the composite image and the transmission image to mask each drop image. The remaining image portion that is not masked is compared with a threshold to thereby detect a defect.

(Inspection Algorithm 3)

Primary differentiation processing is performed on an image signal representing the composite image and an image signal representing the transmission image, respectively. A logical OR between two primary-differentiated signals is obtained and an image portion corresponding to each drop image is excluded from an inspection target.

Figure 4:
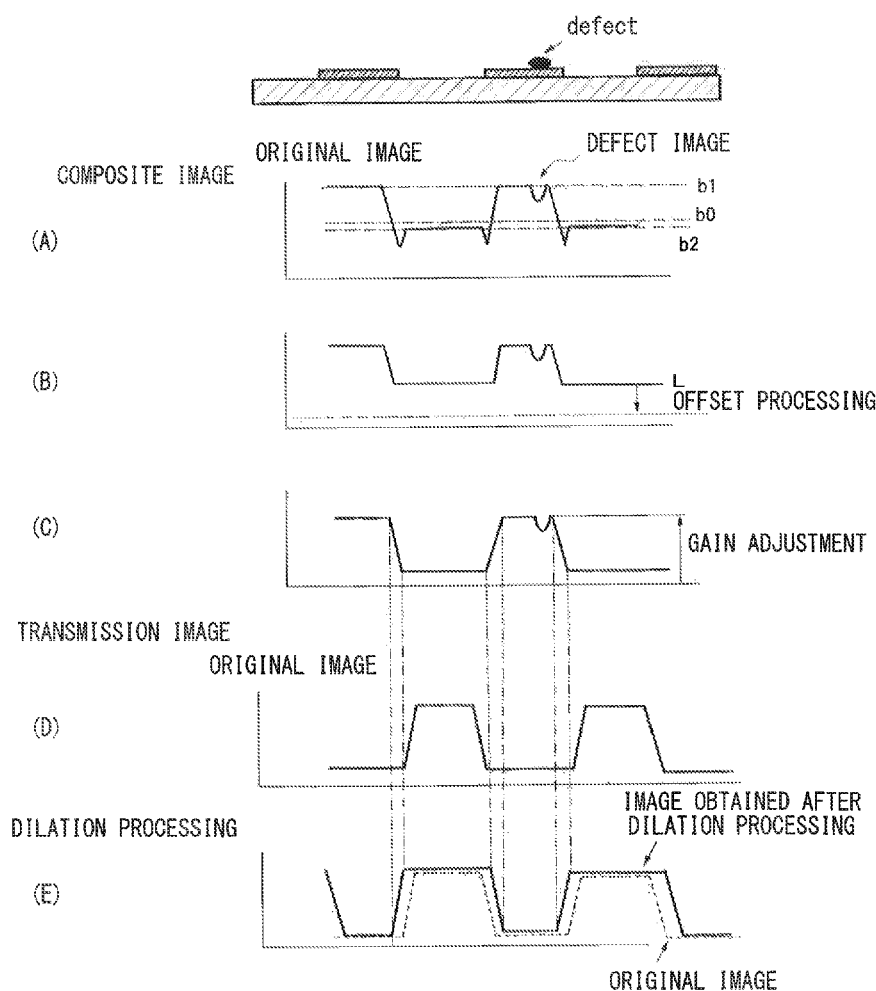
FIGS. 4(A) to 4(E) are diagrams showing signal forms in a first inspection algorithm.

The inspection algorithm 1 will now be described. FIGS. 4A to 4E and FIG. 5 each show a mode for processing image signals in the inspection algorithm 1. FIG. 4A shows the composite image signal output from the second image pickup element 18. In this embodiment, signal processing for deleting the transmission image and the drop image from the composite image is performed by limiter processing. Since the limiter processing for deleting the drop image is carried out, when the composite image is formed in the present invention, the illumination optical system is set so as to form a difference between the luminance level of the image of the pattern portion and the luminance level of the image of the light-transmitting portion. Specifically, when the luminance value of the image of the pattern portion in the composite image is b1 and the luminance value of the image of the light-transmitting portion is b2, the illumination optical system is set so as to satisfy b2<b1. More specifically, the signal intensity level of light output from the pattern portion is set to about 200 levels of 256 gray scales, and the signal intensity level of light output from the light-transmitting portion is set to about 150 levels. By providing a difference between the signal levels in this manner, the image of the pattern portion and the image of the light-transmitting portion are distinguished from each other in the image signal. Further, when the luminance value of the limit level in the limiter processing is b0, the level of the limiter processing is set so as to satisfy b2<b0<b1. Furthermore, in the limiter processing, luminance values of pixels having a luminance value equal to or smaller than the luminance value b0 of the limit level are deleted or uniformly converted into a signal indicating a luminance value equal to or smaller than the luminance value b1. In this embodiment, luminance values of pixels having a luminance value equal to or smaller than the luminance value b0 are uniformly converted into a signal indicating the luminance value b0. By this limiter processing, the transmission image and the drop image are deleted from the composite image. FIG. 4B shows the composite image subjected to the limiter processing.

Next, offset adjustment processing is executed on the composite image signal subjected to the limiter processing. In this offset adjustment processing, the signal level of the composite image subjected to the limiter processing is adjusted so as to match a predetermined reference level. For example, the signal level is adjusted so that the amount of offset from the reference signal level of the signal level of the image portion subjected to the limiter processing matches a predetermined offset amount.

Next, gain adjustment processing is executed on the composite image signal subjected to the offset processing. In this gain adjustment, for example, the gain is adjusted so that the difference in luminance value between the luminance value of the image of the pattern portion and the limit value substantially matches the difference between the luminance value of the image of the light-transmitting portion in the transmission image and the luminance value of the image of the pattern portion. FIG. 4C shows the composite image signal subjected to the gain adjustment.

Next, dilation processing is performed on the edge of the image of the light-transmitting portion in the transmission image. The size of the image portion subjected to the limiter processing in the composite image is reduced by the amount corresponding to the number of pixels corresponding to the drop image. Therefore, there is no symmetry between the composite image subjected to the limiter processing and the original transmission image. When these images are added, a discontinuity occurs at the edge of the light-transmitting portion. For this reason, dilation processing is performed on the transmission image so that the edge of the light-transmitting portion is dilated by one to several pixels. Examples of the dilation processing may include dilation processing for replacing the luminance value of the central pixel with a largest luminance value by using a matrix of 3×3 pixels. FIG. 4E shows the transmission image obtained after the dilation processing.

Figure 5:
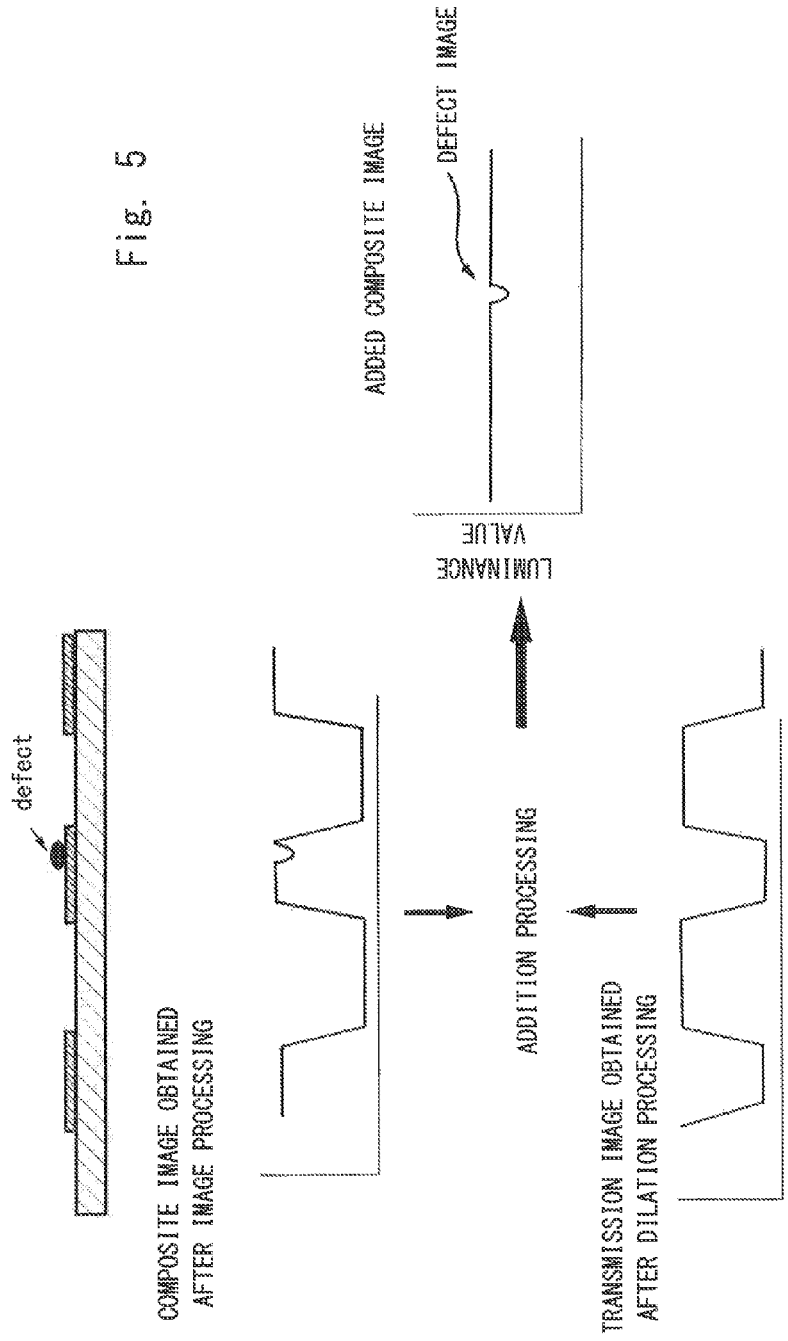
FIG. 5 is a diagram showing signal forms in the first inspection algorithm.

Next, as shown in FIG. 5, addition processing for adding the composite image subjected to the offset and gain adjustment and the transmission image subjected to the dilation processing is performed to thereby form an added composite image. As a result of the execution of the offset processing and the gain adjustment processing, the luminance value of the image of the light-transmitting portion and the luminance value of the image of the pattern portion substantially match each other in the added composite image. This makes it possible to detect a defect by performing the threshold comparison inspection on the added composite signal. Specifically, a defect image can be detected by comparing the added composite signal with a first threshold and determining whether the difference therebetween exceeds a second threshold. In this manner, the limiter processing for deleting the image of the light-transmitting portion and the drop image is performed on the composite image and the composite image subjected to the limiter processing is added to the transmission image, thereby achieving the defect inspection that is not affected by the drop image.

Figure 6:
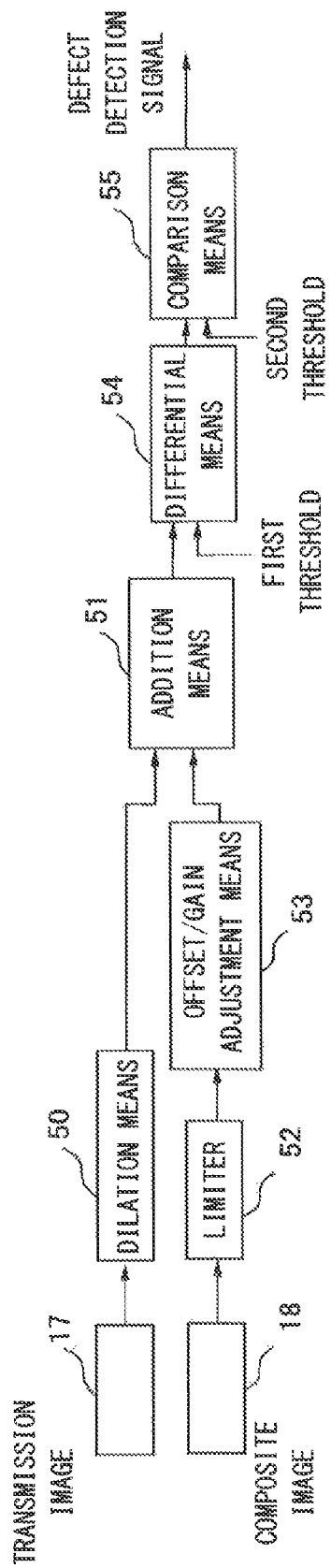
FIG. 6 is a diagram showing signal processing in the first inspection algorithm.

FIG. 6 shows signal processing in the inspection algorithm 1. Assume that signal processing for establishing synchronization is performed on the image signals output from the first and second image pickup elements. The image signal output from the first image pickup element 17, which picks up the transmission image of the photomask to be inspected, is supplied to dilation means 50 so that the edge of the image of the light-transmitting portion of the transmission image is dilated by one to several pixels. The image signal subjected to the dilation processing is supplied to addition means 51. The image signal output from the second image pickup element 18, which picks up the composite image of the photomask, is supplied to limiter means 52 and is subjected to limiter processing. The image signal subjected to the limiter processing is supplied to offset/gain adjustment means 53 and is subjected to an offset adjustment and a gain adjustment. The image signal subjected to the offset and gain adjustment is supplied to the addition means 51.

The addition means 51 adds the transmission image signal subjected to the dilation processing and the composite image signal subjected to the limiter processing and the offset/gain adjustment, to thereby form the added composite signal. The added composite signal is supplied to differential means 54 to detect the difference between the added composite signal and the first threshold. The detected difference value is supplied to comparison means 55. The comparison means 55 compares the detected difference value with the second threshold. When the difference value exceeds the second threshold, the comparison means 55 determines that a defect is present, and generates a defect detection signal. The defect detection signal, as well as corresponding address information, is supplied to a memory, and the defect and the address thereof are stored into the memory. In this case, the image of the defect can be stored into another memory. The storage of the defect image into the memory allows display and review of the defect image on a monitor.

Next, the inspection algorithm 2 will be described with reference to FIGS. 7A to 7D and FIG. 8. In the second inspection algorithm, masking processing is performed on the image signal having a luminance value equal to or smaller than a predetermined threshold in at least the pattern portion of the transmission image formed by the first image pickup element, and the defect detection is made for the image of the light-transmitting portion of the photomask. Further, masking processing is performed on the image signal having a luminance value equal to or smaller than a predetermined threshold of the composite image formed by the second image pickup element, and the defect detection is made for the image of the pattern portion of the photomask. Specifically, in this embodiment, when the luminance value of the image of the light-transmitting portion of the transmission image is a1; the luminance value of the image of the pattern portion is a2; and the masking level is a0, the masking level is set so as to satisfy a2<a0<a1. Further, a region with a luminance value equal to or smaller than a0 is subjected to dilation processing by several pixels, and a portion including a pattern portion and an edge portion of the pattern portion is masked, thereby using only the image of the light-transmitting portion of the transmission image as the target of the defect detection. More specifically, a defect in the light-transmitting portion except the edge portion is detected.

In the composite image, when the luminance value of the image of the pattern portion is b1 and the luminance value of the image of the light-transmitting portion is b2, the illumination optical system is set so as to satisfy b2<b1 and the masking level b0 is set so as to satisfy b2<b0<b1. Further, a region with a luminance value equal to or smaller than b0 is subjected to dilation processing by several pixels, and a portion including a light-transmitting portion and an edge portion of the light-transmitting portion is masked, thereby selectively using only the image of the pattern portion of the composite image as the target of the detect detection. More specifically, a defect in the pattern portion except the edge portion is detected.

By setting the levels in this manner, the defect detection in the light-transmitting portion of the photomask can be performed based on the transmission image, and the defect detection in the pattern portion can be performed based on the composite image. As a result, the defect detection that is not affected by the drop image can be achieved while utilizing the properties inherent in the composite image having a high resolution in the vicinity of the edge portion of the pattern portion.

Limiter processing can be performed instead of the masking processing. Specifically, the masking levels a0 and b0 are set as limiter levels, and a region with a luminance value equal to or smaller than a0 is subjected to dilation processing by several pixels, thereby deleting only an image including a pattern portion and an edge portion of the pattern portion. Further, in the composite image, a region with a luminance value equal to or smaller than b0 is subjected to dilation processing by several pixels, thereby deleting only an image including a light-transmitting portion and an edge portion of the light-transmitting portion. Then the detect detection can be made for the remaining image portion. In this case, the defect detection is made for an image portion (pattern portion) having a luminance value exceeding the luminance value b0 in the composite image, and the defect detection is made for an image portion (light-transmitting portion) having a luminance value exceeding the luminance value a0 in the transmission image.

Note that the luminance values a0 and b0 are set to, for example, luminance values in the edge portion of the pattern portion.

Figure 7:
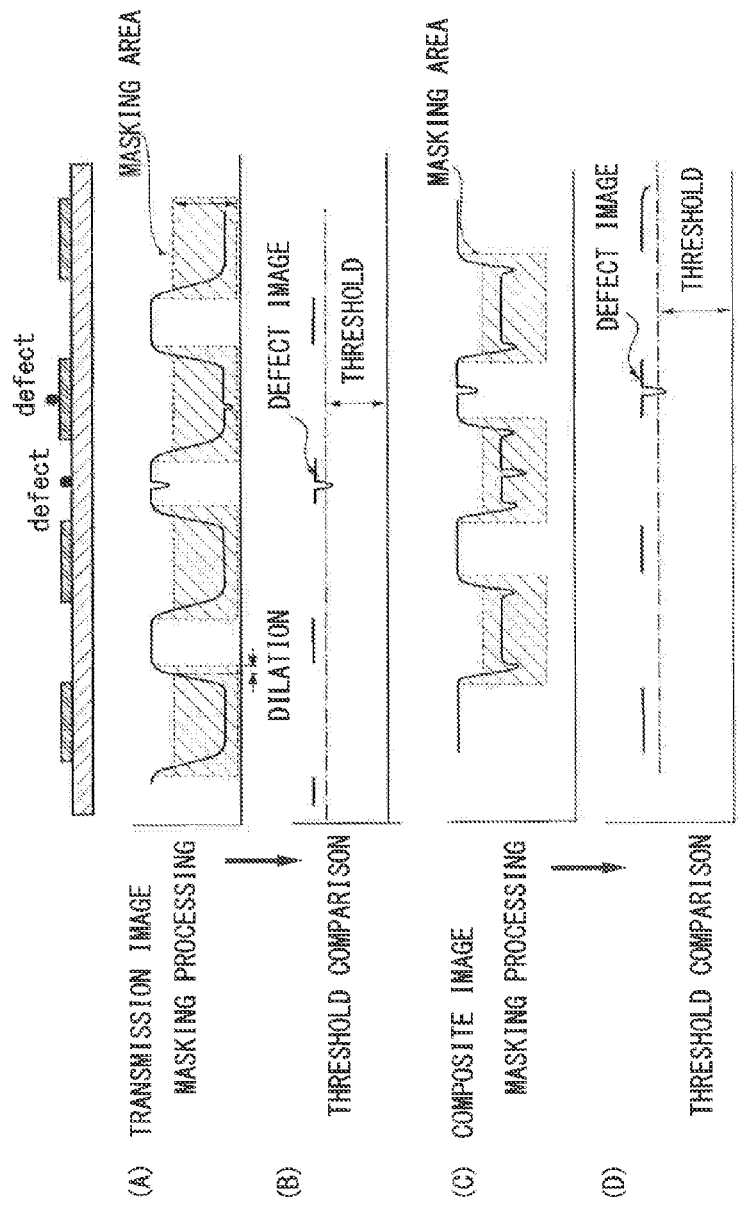
FIGS. 7(A) to 7(D) are diagrams showing signal forms in a second inspection algorithm.

FIG. 7A shows an image signal representing the transmission image output from the first image pickup element. The hatching area in FIG. 7A represents an area to be masked. FIG. 7B shows the transmission image obtained after masking processing. FIG. 7C shows an image signal representing the composite image output from the second image pickup element and an area to be masked. FIG. 7D shows the composite image obtained after masking processing. Note that the threshold for use in the masking processing can be set based on a result obtained by preliminarily picking up a transmission image and a composite image of a photomask to be inspected by an operator.

Figure 8:
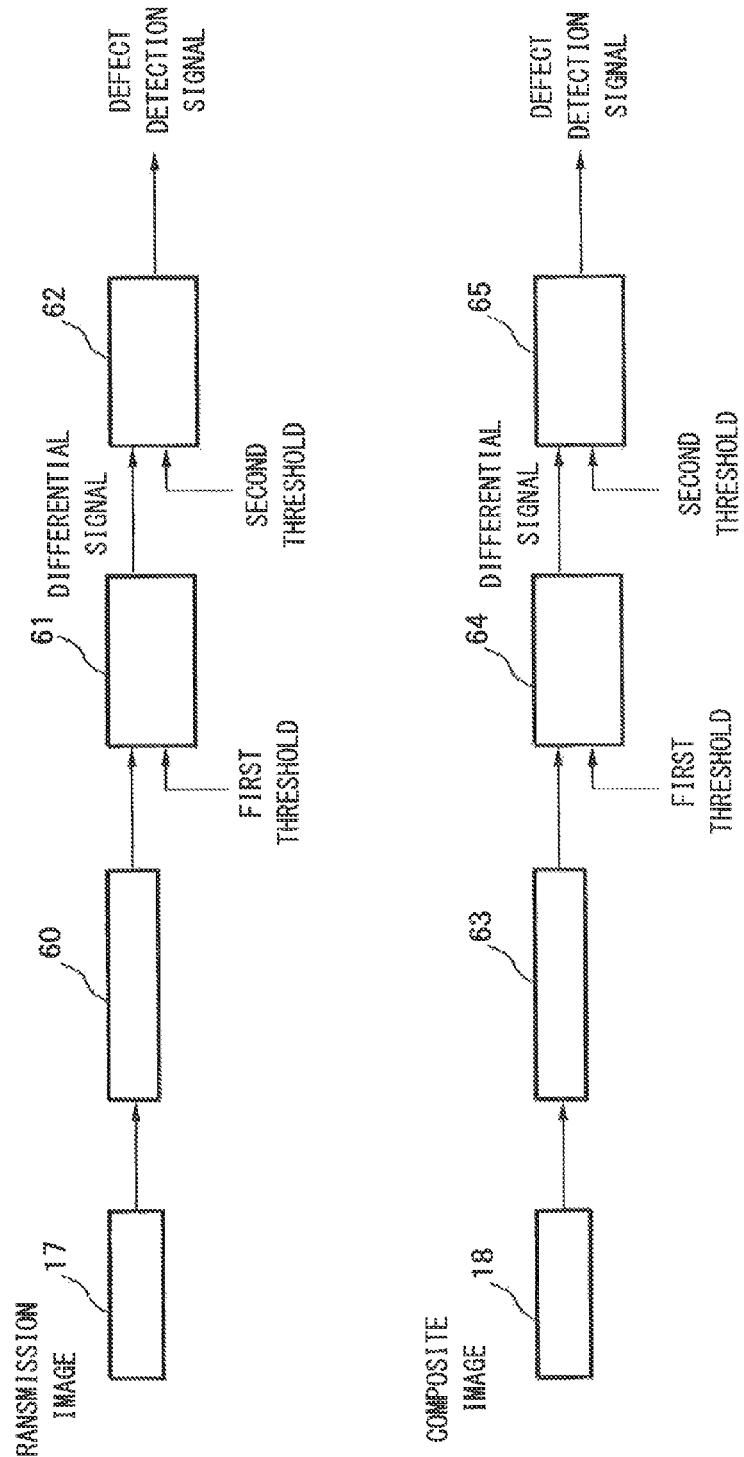
FIG. 8 is a diagram showing signal processing in the second inspection algorithm.

FIG. 8 shows signal processing in the inspection algorithm 2. The image signal representing the transmission image output from the first image pickup element 17 is supplied to first masking means 60, and an image having a luminance value equal to or smaller than a predetermined luminance value is subjected to dilation processing by several pixels, and then, the portion subjected to the dilation processing is masked. The masked image signal is supplied to primary differential means 61, and a difference value from the first threshold is formed and output as a differential signal. This differential signal is supplied to a first comparator 62. When the difference value exceeds the predetermined threshold, it is determined that a defect is present, and the defect detection signal is generated. By this processing, the defect inspection is performed on the light-transmitting portion of the photomask.

The image signal representing the composite image output from the second image pickup element 18 is supplied to second masking means 63, and an image having a luminance value equal to or smaller than a predetermined luminance value is subjected to dilation processing by several pixels, and then, the portion subjected to the dilation processing is masked. The image signal subjected to the masking processing is supplied to second differential means 64, and a difference value from the second threshold is formed and output as a differential signal. This differential signal is supplied to a second comparator 65. When the difference value exceeds the predetermined threshold, it is determined that a defect is present, and the defect detection signal is generated. By this processing, the defect inspection is performed on the pattern portion of the photomask. The inspection algorithm based on the masking processing shown in FIG. 8 allows the transmission image and the composite image to be inspected separately.

Figure 9:
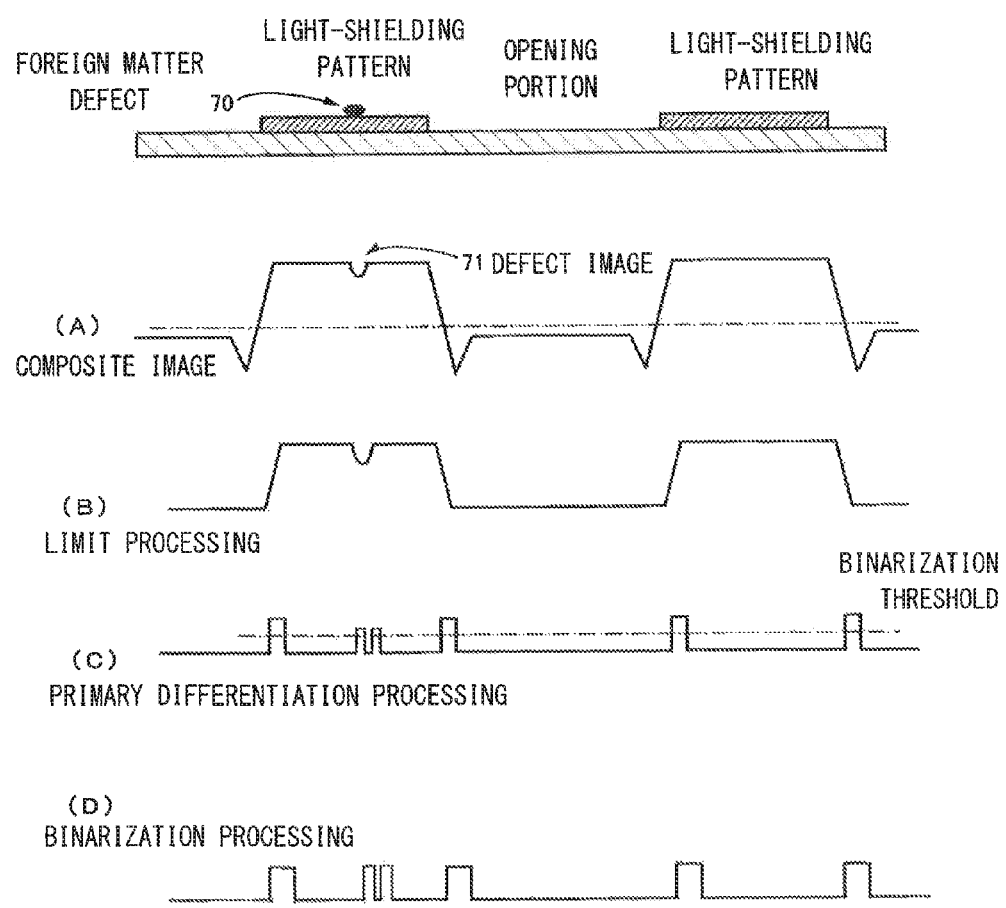
FIGS. 9(A) to 9(D) are diagrams showing signal forms in a third inspection algorithm.

Next, the inspection algorithm 3 will be described. In the inspection algorithm 3, the primary differentiation processing is respectively performed on the image signal, which represents the transmission image and is output from the first image pickup element, and the image signal, which represents the composite image and is output from the second image pickup element, and processing for excluding a variation in luminance at each pattern edge from the inspection target is performed. First, an embodiment in which a defect present in the pattern portion is detected will be described. The composite image signal is used as a test signal to be inspected, and the signal representing the transmission image is used as a reference signal. FIGS. 9A to 9D each show a mode of signal processing for the composite image output from the second image pickup element. FIGS. 10A to 10G each show a mode of signal processing for the transmission image output from the first image pickup element. Note that synchronous processing is performed on the output signals from the first and second image pickup elements, and thus the output signals are synchronous with each other. In this embodiment, a half-tone type phase shift mask (EPSM) in which drop images are relatively prominently generated in the composite image is used as the photomask to be inspected. FIG. 9A shows the original composite image output from the second image pickup element. The illumination system for forming the composite image is set so that the luminance value b1 of the image of the pattern portion is larger than the luminance value b2 of the image of the light-transmitting portion, i.e., b2<b1 is satisfied. In this embodiment, assume that a foreign matter defect 70 is present on the pattern portion. Accordingly, a defect image 71 having a low luminance is generated in the composite image of the corresponding pattern portion.

Limiter processing is performed on the original composite image signal to delete the drop image. In this case, the threshold level b0 of the limiter processing is set so as to satisfy b2<b0<b1, and image signals having a luminance value equal to or smaller than the luminance value b0 are uniformly converted into a signal representing the luminance value b0. FIG. 9B shows the composite image signal obtained after the limiter processing. Note that the limiter processing, which is processing for deleting the drop image, is carried out as needed, and thus is not essential for the present invention.

Next, the primary differentiation processing is performed on the composite image signal subjected to the limiter processing. FIG. 9C shows the composite image signal obtained after the primary differentiation processing. The edge portion of the pattern portion is detected by the primary differentiation processing. At the same time, since the foreign matter defect is a defect image having a low luminance, the edge portion of the defect image is also detected by the primary differentiation processing.

A binarization threshold level is set to the signal subjected to the primary differentiation processing, and binarization processing is performed on the signal. FIG. 9D shows the signal obtained after the binarization processing. As shown in FIG. 9D, the edge portion of the pattern portion and the edge portion of the defect image, which cause a variation in luminance, are detected as "1", and the other signal portion is detected as "0".

Figure 10:
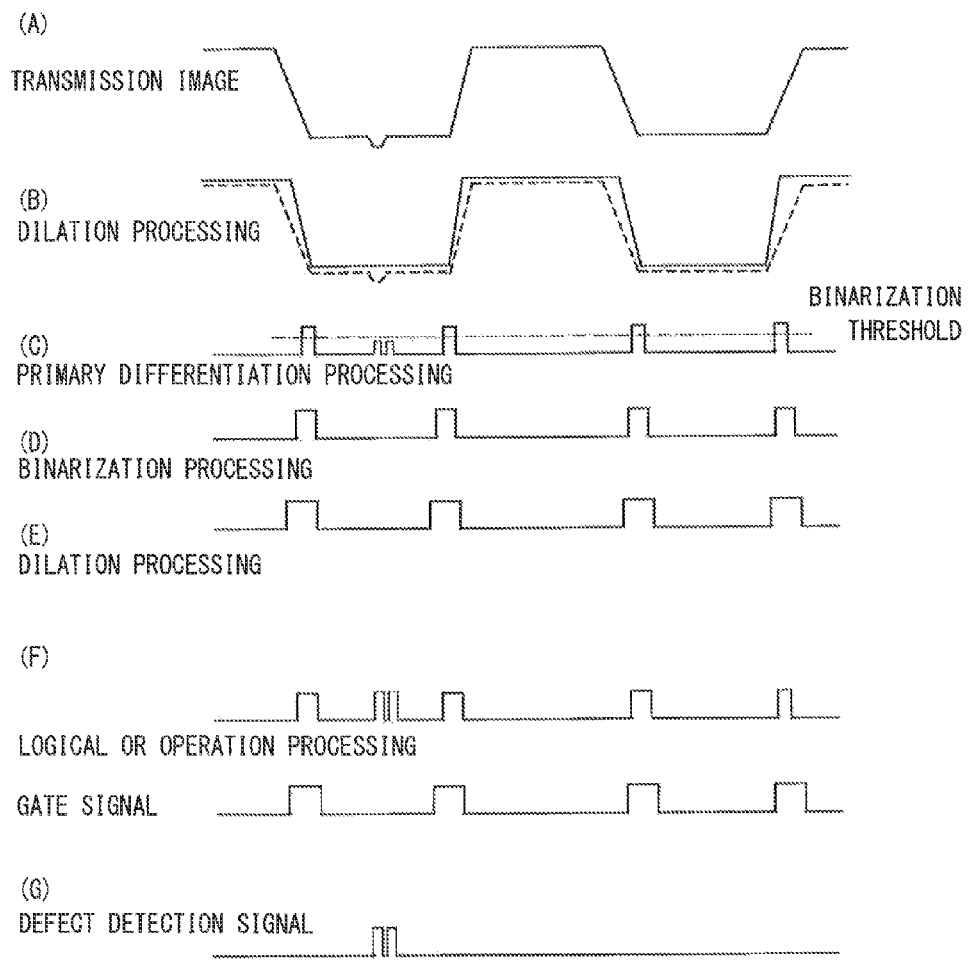
FIGS. 10(A) to 10(G) are diagrams showing signal forms in the third inspection algorithm.

The following signal processing is performed also on the transmission image signal, which is a reference signal, along with the signal processing for the composite image. FIG. 10A shows the signal form of the transmission image. In the transmission image signal, a minute low-luminance image corresponding to the defect image is formed.

First, dilation processing is performed on the image of the light-transmitting portion of the transmission image signal. As the dilation processing, for example, dilation processing for replacing the luminance value of the central pixel with the largest luminance value is performed on a matrix of 3×3 pixels. In FIG. 10B, the dashed line represents the original transmission image signal, and the solid line represents the transmission image signal subjected to the dilation processing. Note that the dilation processing is carried out as needed, and thus is not signal processing essential for the present invention.

Primary differentiation processing is performed on the transmission image signal subjected to the dilation processing. FIG. 10C shows the transmission image signal subjected to the primary differentiation processing. By the primary differentiation processing, the edge portions of the light-transmitting portion and the pattern portion and the edge portion of the defect image are detected.

Binarization processing is executed on the transmission image signal subjected to the primary differentiation processing. In the binarization processing, the binarization threshold is set to a relatively high value. Accordingly, a variation in luminance of the defect image is relatively small and is smaller than the binarization threshold, so that the defect image is deleted in the binarization processing. As a result, only the variation in luminance of the edge portion of the pattern portion is detected as a logic "1".

Dilation processing is performed again, as needed, on the transmission image signal subjected to the binarization processing, thereby dilating or extending the region represented by the logic "1". As the dilation processing, dilation processing in which a matrix of 3×3 pixels is also used can be performed.

A binarized signal subjected to the dilation processing is used as a gate signal for the test signal. Specifically, a binarized signal for testing, which is created for the composite image signal, and a binarized signal for reference, which is created from the transmission image signal and functions as a gate signal, are supplied to gate means. Logical operation processing corresponding to an exclusive OR operation is executed on the binarized signal for testing. FIG. 10F shows the signal processing. In the logical operation processing, the binarized signal for testing and the binarized signal for reference, each of which corresponds to the edge portion of the pattern portion, are substantially simultaneously generated. When the binarized signal for reference serving as the gate signal is input, the signal for testing is set to the logic "0". This logical operation processing allows the binarized signal corresponding to the edge portion of the pattern portion to be deleted from the binarized signal for testing, and allows only the binarized signal corresponding to the defect image to be output. Accordingly, the test signal obtained after the logical operation processing forms the defect detection signal indicating the presence of a defect. As a result, the defect present in the pattern portion is detected.

Note that the limiter processing and the dilation processing are processing to be carried out to prevent a malfunction from occurring when a deviation between the test signal and the reference signal occurs. Therefore, the limiter processing and the dilation processing are not essential for the present invention.

In the case of detecting a defect present in the light-transmitting portion, the transmission image signal output from the first image pickup element 17, which picks up the transmission image, is used as the test signal, and the composite image signal output from the second image pickup element 18, which picks up the composite image, is used as the reference signal. That is, the binarized signal obtained by performing the primary differentiation processing and the binarization processing on the composite image signal is used as the gate signal.

Figure 11:
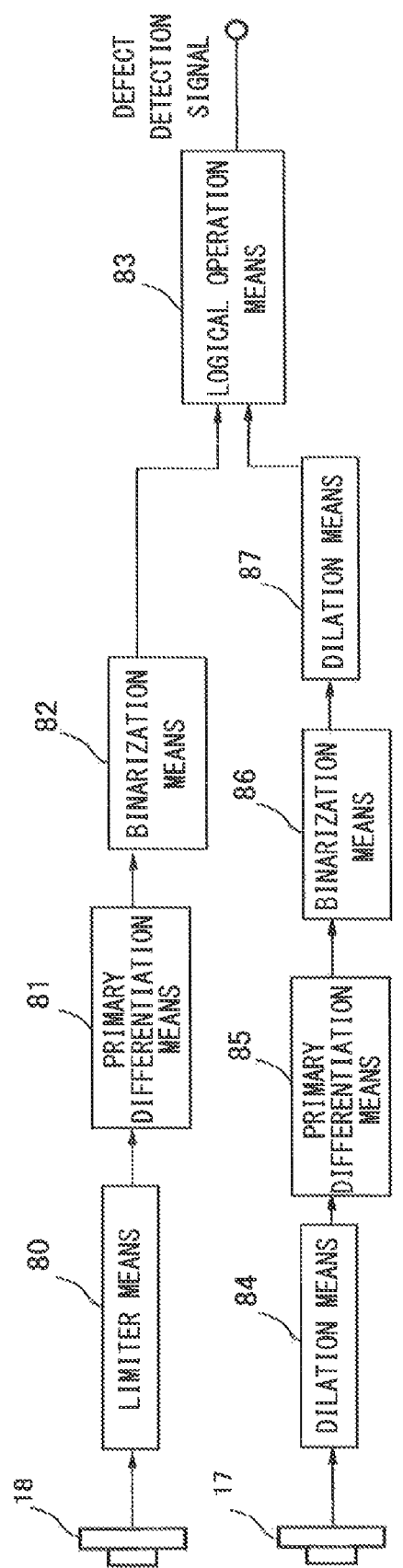
FIG. 11 is a diagram showing signal processing in the third inspection algorithm.

FIG. 11 shows signal processing in the inspection algorithm 3. The image signal that represents the composite image and is output from the second image pickup element 18 serves as a test signal. The test signal is supplied to limiter means 80 and is subjected to limiter processing for replacing pixels having a luminance value equal to or smaller than a predetermined limiter threshold with limiter values. The signal subjected to the limiter processing is supplied to primary differentiation means 81 and is subjected to the primary differentiation processing. The obtained primary-differentiated signal is supplied to binarization means 82, and the binarized signal is output. The generated binarized signal for testing is supplied to logical operation means 83.

The image signal that represents the transmission image and is output from the first image pickup element 17 serves as the reference signal. The image signal is supplied to dilation means 84 and is subjected to predetermined dilation processing. The signal subjected to dilation limiter processing is supplied to primary differentiation means 85 and is subjected to the primary differentiation processing. The obtained primary-differentiated signal is supplied to binarization means 86, and the binarized signal is output. The generated binarized signal for reference is supplied to the logical operation means 83.

The logical operation means 83 receives the binarized signal for testing generated from the composite image signal and the binarized signal for reference generated from the transmission image signal. The logical operation means 83 performs signal processing similar to an exclusive OR operation. When the binarized signal for testing indicates "1" and the binarized signal for reference indicates "1", the binarized signal for testing is converted to "0" and the binarized signal for testing is output. In the other cases, the binarized signal for testing is directly output. Specifically, the logical operation means 83 uses the binarized signal for reference as the gate signal, and when the gate signal represents a logic "1", the logical operation means 83 changes the logic of the test signal to the logic "0" and outputs the test signal. By this signal processing, the defect detection signal representing a defect shown in FIG. 10G is output, and the defect present in the pattern portion can be detected.

In the inspection for the light-transmitting portion of the photomask, the image signal output from the first image pickup element 17, which outputs the transmission image signal, is used as the test signal, and the image signal output from the second image pickup element 18, which outputs the composite image signal, is used as the reference signal. That is, the primary differentiation processing and the binarization processing are performed on the transmission image signal output from the first image pickup element, and the transmission image signal is supplied to the logical operation means. Further, the primary differentiation processing and the binarization processing are performed on the composite image signal output from the second image pickup element, and the composite image signal is supplied to the logical operation means. The logical operation means uses the binarized signal, which is generated based on the composite image signal output from the second image pickup element, as the gate signal, and sets the corresponding test signal to the logic "0" when the gate signal represents the logic "1". Thus, the provision of two signal processing systems shown in FIG. 11 enables detection of a defect present in the pattern portion and a defect present in the light-transmitting portion in parallel.

The present invention is not limited to embodiments described above, but can be modified or altered in various manners. While the above embodiments illustrate the case where a single die is formed on a photomask, for example, when a plurality of dies are formed on a photomask, a defect can be detected based on a die-to-die comparison inspection algorithm using a transmission image and a composite image.

What is claimed is:

1. An inspection apparatus that inspects a photomask having a pattern forming surface on which a pattern portion and a light-transmitting portion are formed, and a back surface opposed to the pattern forming surface, the inspection apparatus comprising:

an illumination optical system including: a transmitted illumination optical system that projects a transmitted illumination beam toward a back surface of a photomask to be inspected and illuminates a first area of the photomask; and a reflected illumination optical system that projects a reflected illumination beam toward an element forming surface of the photomask and illuminates a second area of the photomask, the second area being smaller than the first area and overlapping the first area in an optical axis direction;

a detection system including: a first image pickup element that receives synthetic light of reflected light and transmitted light output from the second area of the photomask and picks up a composite image obtained by optically synthesizing a transmission image and a reflection image of the photomask; and a second image pickup element that receives transmitted light output from a third area of the photomask and picks up a transmission image of the photomask, the third area being a remaining area of the first area excluding the second area; and a signal processing device that is coupled to the detection system, processes an image signal output from the detection system, and outputs data indicating a defect, wherein the transmitted illumination optical system and the reflected illumination optical system are set so as to satisfy $b2 < b1$, when a luminance value of an image of the pattern portion of the composite image is $b1$ and a luminance value of an image of the light-transmitting portion is $b2$, and the signal processing device includes:

a limiter processing unit that performs limiter processing on an image signal output from the first image pickup element to delete a signal portion having a luminance value equal to or smaller than a luminance value $b0$ that satisfies $b2 < b0 < b1$, or uniformly convert the signal portion into a signal having a luminance value equal to or smaller than a luminance value $b1$; and a defect detection unit that detects a defect by using a signal subjected to the limiter processing and an image signal output from the second image pickup element.

2. The inspection apparatus according to claim 1, wherein the signal processing device includes:

a dilation processing unit that performs, for the image signal output from the second pickup element, dilation processing on an edge of an image corresponding to the light-transmitting portion;

an addition unit that adds a signal subjected to the limiter processing and a signal subjected to the dilation processing, and outputs an added composite signal; and a comparison unit that compares the added composite signal with a threshold.

3. The inspection apparatus according to claim 2, wherein the illumination optical system includes an adjustment unit that adjusts a ratio between an intensity of transmitted illumination light incident on the second area and an intensity of transmitted illumination light incident on the third area.

4. The inspection apparatus according to claim 1, wherein one of a binary type photomask, a half-tone type photomask, and a tri-tone type photomask is used as the photomask.

5. The inspection apparatus according to claim 1, wherein the signal processing device includes an offset/gain adjustment processing unit provided at a subsequent stage of the limiter processing unit, performs offset adjustment processing and gain adjustment processing on the signal subjected to the limiter processing, and supplies the signal to the addition unit.

6. An inspection apparatus that inspects a photomask having a pattern forming surface on which a pattern portion and a light-transmitting portion are formed, and a back surface opposed to the pattern forming surface, the inspection apparatus comprising:
an illumination optical system including: a transmitted illumination optical system that projects a transmitted illumination beam toward a back surface of a photomask to be inspected, and illuminates a first area of the photomask; and a reflected illumination optical system that projects a reflected illumination beam toward an element forming surface of the photomask, and illuminates a second area of the photomask, the second area being smaller than the first area and overlapping the first area in an optical axis direction;
a detection system including: a first image pickup element that receives synthetic light of reflected light and transmitted light output from the second area of the photomask, and picks up a composite image obtained by optically synthesizing a transmission image and a reflection image of the photomask; and a second image pickup element that receives transmitted light output from a third area of the photomask and picks up a transmission image of the photomask, the third area being a remaining area of the first area excluding the second area; and
a signal processing device that is coupled to the detection system, processes an image signal output from the detection system, and outputs data indicating a defect, wherein
the transmitted illumination optical system and the reflected illumination optical system are set so as to satisfy $b2<b1$, when a luminance value of an image of the pattern portion of the composite image is b1 and a luminance value of an image of the light-transmitting portion is b2, and
the signal processing device includes:
a first masking unit that masks, in the transmission image, an image portion having a luminance value equal to or smaller than a predetermined luminance value a0 that satisfies $a2<a0<a1$, when a luminance value of an image of the light-transmitting portion is a1 and a luminance value of an image of the pattern portion is a2;
a second masking unit that masks, in the composite image, an image portion having a luminance value equal to or smaller than a predetermined luminance value b0 that satisfies $b2<b0<b1$;
a first defect detection unit that compares an image signal subjected to the first masking processing with a first threshold; and
a second defect detection unit that compares an image signal subjected to the second masking processing with a second threshold.

7. The inspection apparatus according to claim 6, wherein dilation processing is performed on a region with a luminance value equal to or smaller than the predetermined threshold a0, thereby allowing the first masking unit to mask an image of a portion corresponding to the pattern portion and an edge portion thereof in the transmission image, and
dilation processing is performed on a region with a luminance value equal to or smaller than the predetermined threshold b0, thereby allowing the second masking unit to mask an image corresponding to the light-transmitting portion and an edge portion thereof in the composite image.

8. The inspection apparatus according to claim 6, wherein the illumination optical system includes an adjustment unit that adjusts a ratio between an intensity of transmitted illumination light incident on the second area and an intensity of transmitted illumination light incident on the third area.

9. The inspection apparatus according to claim 6, wherein one of a binary type photomask, a half-tone type photomask, and a tri-tone type photomask is used as the photomask.

10. An inspection apparatus that inspects a photomask having a pattern forming surface on which a pattern portion and a light-transmitting portion are formed, and a back surface opposed to the pattern forming surface, the inspection apparatus comprising:
an illumination optical system including: a transmitted illumination optical system that projects a transmitted illumination beam toward a back surface of a photomask to be inspected, and illuminates a first area of the photomask; and a reflected illumination optical system that projects a reflected illumination beam toward an element forming surface of the photomask, and illuminates a second area of the photomask, the second area being smaller than the first area and overlapping the first area in an optical axis direction;
a detection system including: a first image pickup element that receives synthetic light of reflected light and transmitted light output from the second area of the photomask, and picks up a composite image of a transmission image and a reflection image of the photomask; and a second image pickup element that receives transmitted light output from a third area of the photomask and picks up a transmission image of the photomask, the third area being a remaining area of the first area excluding the second area; and
a signal processing device that is coupled to the detection system, processes an image signal output from the detection system, and outputs data indicating a defect, wherein
the transmitted illumination optical system and the reflected illumination optical system are set so as to satisfy $b2<b1$, when a luminance value of an image of the pattern portion of the composite image is b1 and a luminance value of an image of the light-transmitting portion is b2, and
the signal processing device includes:
first and second differentiation processing units that respectively form first and second primary-differentiated signals by performing primary differentiation processing on a composite image signal and a transmission image signal;
first and second binarization processing units that respectively form first and second binarized signals by performing binarization processing on the first and second primary-differentiated signals;

a first logical operation unit that performs a first logical operation on the first binarized signal by using the second binarized signal as a gate signal, setting the first binarized signal to a logic "0" when the second binarized signal represents a logic "1", and outputting the first binarized signal as a defect detection signal; and a second logical operation unit that performs a second logical operation on the second binarized signal by using the first binarized signal as a gate signal, setting the second binarized signal to the logic "0" when the first binarized signal represents the logic "1", and outputting the second binarized signal as the defect detection signal.

11. The inspection apparatus according to claim 10, wherein the first logical operation unit outputs the defect detection signal representing a defect present in the pattern portion, and the second logical operation unit outputs the defect detection signal representing a defect present in the light-transmitting portion.

12. The inspection apparatus according to claim 10, wherein the illumination optical system includes an adjustment unit that adjusts a ratio between an intensity of transmitted illumination light incident on the second area and an intensity of transmitted illumination light incident on a third area.

13. The inspection apparatus according to claim 10, wherein one of a binary type photomask, a half-tone type photomask, and a tri-tone type photomask is used as the photomask.

14. An inspection method that inspects a photomask having a pattern portion and a light-transmitting portion, the pattern portion and the light-transmitting portion being formed on a transparent substrate, the inspection method comprising:

forming a transmission image of a photomask to be inspected;

forming a composite image obtained by optically synthesizing a transmission image and a reflection image of the photomask, the composite image being set so as to satisfy $b2<b1$, when a luminance value of an image of the pattern portion is $b1$ and a luminance value of an image of the light-transmitting portion is $b2$;

a limiter step of deleting, in the composite image, an image portion having a luminance value equal to or smaller than a predetermined luminance value $b0$ that satisfies $b2<b0<b1$, or uniformly converting the image portion into a signal representing a luminance value equal to or smaller than the luminance value $b1$; and detecting a defect based on the composite image subjected to the limiter processing and the transmission image.

* * * * *